United States Patent

Briggs et al.

[11] Patent Number: 5,858,340
[45] Date of Patent: *Jan. 12, 1999

[54] COSMETIC COMPOSITIONS

[75] Inventors: Gillian Scott Briggs, Egham Surrey; Robert Francis Date, Woking Surrey; Marie-Isabelle Moine, Richmond on Thames Surrey, all of England

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 534,601

[22] Filed: Sep. 27, 1995

Related U.S. Application Data

[63] Continuation of Ser. No. 341,549, Nov. 21, 1994, abandoned.

[30] Foreign Application Priority Data

May 22, 1992 [GB] United Kingdom .................. 9210966

[51] Int. Cl.$^6$ ................................. A16K 7/00; A16K 7/06
[52] U.S. Cl. .................................... 424/70.19; 424/78.03; 424/70.11; 424/70.12; 424/70.16; 424/401; 514/944; 514/975
[58] Field of Search ................................. 424/401, 78.03, 424/70.11, 70.12, 70.16, 70.19; 514/944, 975

[56] References Cited

U.S. PATENT DOCUMENTS

| | | | |
|---|---|---|---|
| 4,686,254 | 8/1987 | Lochhead et al. | 524/99 |
| 4,690,818 | 9/1987 | Puchalski, Jr. et al. | 424/70 |
| 4,719,099 | 1/1988 | Grollier et al. | 424/47 |
| 4,837,019 | 6/1989 | Georgalas | 424/101 |
| 4,863,725 | 9/1989 | Deckner | 424/81 |
| 4,883,659 | 11/1989 | Goodman et al. | 424/78 |
| 4,954,532 | 9/1990 | Elliott | 514/846 |
| 5,043,155 | 8/1991 | Puchalski | 424/78 |
| 5,098,699 | 3/1992 | Hayama | 424/71 |
| 5,380,528 | 1/1995 | Alban | 424/401 |

*Primary Examiner*—Sally Gardner-Lane
*Attorney, Agent, or Firm*—Tara M. Rosnell; William J. Winter

[57] ABSTRACT

A skin or hair care composition in the form of an aqueous gel comprising a humectant, a water-soluble polyglycerylmethacrylate lubricant, a hydrophilic gelling agent and a polyethyleneglycol glyceryl fatty ester surfactant. The compositions provide improved moisturization, skin feel and skin care benefits, reduced tack and residue characteristics together with excellent visual clarity, rub-in and absorption characteristics.

20 Claims, No Drawings

COSMETIC COMPOSITIONS

This is a continuation of application Ser. No. 08/341 549, filed on Nov. 21, 1994 now abandoned.

TECHNICAL FIELD

The present invention relates to skin- and hair-care cosmetic compositions. In particular it relates to cosmetic compositions in the form of aqueous gels or lotions which provide improved moisturization, skin feel and skin care benefits, reduced tack and residue characteristics together with excellent visual clarity, rub-in and absorption characteristics.

BACKGROUND OF THE INVENTION

Skin is made up of several layers of cells which coat and protect the keratin and collagen fibrous proteins that form the skeleton of its structure. The outermost of these layers, referred to as the stratum corneum, is known to be composed of 25 nm protein bundles surrounded by 8 nm thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant or solvent to interact with the keratin, creating irritation.

It is now recognised that maintaining the proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue, and the skin begins to scale and becomes itchy. Skin permeability is also decreased somewhat when there is inadequate water across the stratum corneum. On the other hand, too much water on the outside of the skin causes the stratum corneum to ultimately sorb three to five times its own weight of bound water. This swells and puckers the skin and results in approximately a two to three fold increase in the permeability of the skin to water and other polar molecules.

Hair consists of many of the same constituents as the stratum corneum. The outermost region of cells forms a rather thick chemically resistant protective coating enclosing the hair fibre which is called the cuticle. The surface of the cuticle is covered with a thin layer called the epicuticle which is thought to contain lipids and protein. The cuticle envelopes the cortex cells which comprise the major part of the fibre mass. Keratinization takes place in the cortex to build stability into the hair structure.

Thus, a need exists for compositions which will assist the stratum corneum and hair cuticle in maintaining their barrier and water-retention functions at optimum performance in spite of deleterious interactions which the skin and hair may encounter in washing, work, and recreation.

Conventional cosmetic cream and lotion compositions as described, for example, in Sagarin, Cosmetics Science and Technology, 2nd Edition, Vol.I, Wiley Interscience (1972) and Encyclopaedia of Chemical Technology, Third Edition, Volume 7 are known to provide varying degrees of emolliency, barrier and water-retention (moisturizing) benefits. However, they can also suffer serious negatives in terms of skin feel (i.e. they often feel very greasy on the skin) as well as having poor rub-in, absorption and residue characteristics. In the case of hair-care compositions they can also suffer from resoiling negatives.

The present invention therefore provides skin- and hair-care cosmetic compositions which provide improvements in moisturization, absorption, residue, tackiness, skin feel and skin care characteristics and which in particular provide improved short and longer term moisturizing effectiveness, while at the same time avoiding depositing oily residues on the skin.

SUMMARY OF THE INVENTION

Accordingly, in one aspect of the present invention, there is provided a skin- or hair-care composition in the form of an aqueous gel or lotion comprising:

(a) from about 0.5% to about 20% by weight of a polyhydric alcohol humectant, (b) from about 0.1% to about 10% by weight of a water-soluble polyglycerylmethacrylate lubricant, (c) from about 0.1% to about 20% by weight of a hydrophilic gelling agent, and (d) from about 0.1% to about 10% by weight of a polyethyleneglycol glyceryl fatty ester surfactant having the formula (I)

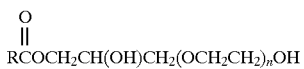

wherein n, the degree of ethoxylation, is from about 2 to about 200, and wherein R comprises an aliphatic radical having from about 5 to about 25 carbon atoms.

The compositions of this aspect of the present invention contain four essential ingredients as well as various optional components as indicated below. All levels and ratios are by weight of total composition, unless otherwise indicated. Chain length and degrees of ethoxylation are also specified on a weight average basis.

A first essential ingredient is a polyhydric alcohol humectant, a preferred humectant being glycerine (sometimes known as glycerol or glycerin). Chemically, glycerine is 1,2,3-propanetriol and is a product of commerce. One large source of the material is in the manufacture of soap. Polyhydric alcohol humectants other than glycerine which can be added herein include sorbitol, propylene glycol, butylene glycol, hexylene glycol, ethoxylated glucose and hexanetriol.

In the present compositions, the polyhydric alcohol humectant is present at a level of from about 0.5% to about 20%, preferably from about 1% to about 10%, more preferably from about 2% to about 5% by weight of composition.

A second essential component is a water-soluble polyglycerylmethacrylate lubricant. In general terms, suitable lubricants include those having a viscosity (neat) of less than about 5000 mPa.s, preferably less than about 2000 mPa.s, lubricants having a viscosity (neat) of at least about 50,000 mPa.s, preferably at least about 80,000 mPa.s, and mixtures thereof (viscosities being measured with a Brookfield RVT at 20° C.). More specifically, a preferred lubricant herein comprises a mixture of a first lubricant component having a viscosity (neat) of from about 200 to about 5000 mPa.s, preferably from about 700 to about 900 mPa.s, and a second lubricant component having a viscosity (neat) of at least about 200,000 mpa.s, preferably at least about 500,000 mpa.s, wherein the weight ratio of first lubricant component to second lubricant component is from about 5:1 to about 1:20, preferably from about 2:1 to about 1:15.

The polyglycerylmethacrylate lubricants which can be used in the compositions of this invention are available under the trademark Lubrajel (RTM) from Guardian Chemical Corporation, 230 Marcus Blvd., Hauppage, N.Y. 11787. In general, Lubrajels can be described as hydrates or clathrates which are formed by the reaction of sodium glycerate with a methacrylic acid polymer. Thereafter, the hydrate or clathrate is stabilized with a small amount of propylene glycol, followed by controlled hydration of the resulting product. Lubrajels are marketed in a number of grades of varying glycerate: polymer ratio and viscosity. Suitable Lubrajels include Lubrajel TW, Lubrajel CG and Lubrajel MS, Lubrajel WA, Lubrajel DV and so-called Lubrajel Oil. Preferred for use herein, however, is Lubrajel Oil which has a typical viscosity of about 800 mPa.s, Lubrajel DV which has a typical viscosity of about 1,100,000 mPa.s and mixtures thereof.

In the present compositions, the polyglycerylmethacrylate lubricant is incorporated at a level of from about 0.1% to about 10%, preferably from about 0.2% to about 8%, and more preferably from about 0.5% to about 6% by weight of composition.

The compositions of the invention also contain a hydrophilic gelling agent at a level preferably from about 0.1% to about 20%, more preferably from about 0.2% to about 2%, and especially from about 0.3% to about 1%. The gelling agent preferably has a viscosity (1% aqueous solution, 20° C., Brookfield RVT) of at least about 4000 mPa.s more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, guar gum, hydroxypropyl guar gum and xanthan gum.

Preferred hydrophilic gelling agents herein, however, are acrylic acid/ethyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980 and Carbopol 981. Carbopol 934 is a water-soluble polymer of acrylic acid crosslinked with about 1% of a polyallyl ether of sucrose having an average of about 5.8 allyl groups for each sucrose molecule. A most preferred polymer is Carbopol 981 which has an average molecular weight of about 1,250,000. Also suitable for use herein are hydrophobically-modified cross-linked polymers of acrylic acid having amphipathic properties available under the Trade Name Carbopol 1342 and Pemulen TR-1 (CTFA Designation: Acrylates/10-30 Alkyl Acrylate Crosspolymer). A combination of the polyalkenyl polyether cross-linked acrylic acid polymer and the hydrophobically modified cross-linked acrylic acid polymer is also suitable for use herein.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The compositions of the invention also contain from about 0.1% to about 10%, preferably from about 1% to about 5%, most preferably from about 2% to about 4% by weight of polyethyleneglycol glyceryl fatty ester surfactant having the formula (I).

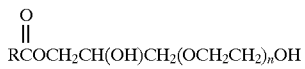

wherein n, the degree of ethoxylation, is from about 2 to about 200, preferably from about 3 to about 80, more preferably from about 5 to about 15, and wherein R comprises an aliphatic radical having from about 5 to about 25 carbon atoms, preferably from about 7 to about 20 carbon atoms.

The weight ratio of water-soluble polyglycerylmethacrylate lubricant to polyethyleneglycol glyceryl fatty ester surfactant in the present composition is from about 5:1 to about 1:10, preferably from about 3:1 to about 1:3.

Suitable glyceryl fatty ester surfactants include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as evening primrose oil, palm oil, almond oil, and corn oil, preferably glyceryl caproate and glyceryl caprylate.

Suitable surfactants of this class are commercially available from Sherex Chemical Co. (Dublin, Ohio, USA) under their Varonic LI line of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PRG 200 glyceryl tallowate), and Varonic LI 63 and 67 (PEG 30 and PEG 80 glyceryl cocoates), and from Croda Inc. (New York, USA) under their Crovol line of materials, such as Crovol A-40 (PEG 20 almond glyceride), Crovol A-70 (PEG 60 almond glyceride), Crovol M-40 (PEG 20 maize glyceride), Crovol M-70 (PEG 60 maize glyceride), Crovol PK-40 (PEG 12 palm kernel glyceride), Crovol PK-70 (PEG 45 palm kernel glyceride) and Crovol EP-70 (PEG 70 evening primrose glyceride). Especially preferred from the viewpoint of moisturizing effectiveness are monocaprylate and monocaproate fatty ester derivatives of polyethylene glycol, or mixtures thereof, particularly materials such as PEG (6) caprylic/capryl glycerate (Softigen 767). Also preferred for use herein are evening primrose derived fatty acid ester surfactants, such as PEG (70) evening primrose glycerides. In preferred embodiments of the invention mixtures of glyceryl fatty ester surfactants are used. Especially preferred embodiments include a mixture of a polyethyleneglycol glyceryl fatty ester surfactant having the formula (I) wherein n is from about 4 to about 20, preferably from about 5 to about 8 and wherein R comprises an aliphatic radical having from about 7 to about 12 carbon atoms and a polyethyleneglycol glyceryl fatty ester surfactant having the formula (I) wherein n is from about 30 to about 50, preferably from about 40 to about 80 and R comprises an aliphatic radical having from about 12 to about 22 carbon atoms, preferably from about 14 to about 20 carbon atoms.

The compositions of the invention are in aqueous gel or lotion form and are preferably formulated so as to have a product viscosity of at least about 4,000 mPa.s and preferably in the range from about 4,000 to about 300,000 mPa.s, more preferably from about 8,000 to about 200,000 mPa.s and especially from about 10,000 to about 50,000 mPa.s (25° C., neat, Brookfield RVT Spindle No. 5). Preferably the compositions are visually clear. The compositions are also preferably substantially free of oil, i.e. contain less than about 1%, and preferably less than about 0.1% of materials which are insoluble or which are not colloidally-soluble in the aqueous gel matrix at 20° C. It is a feature of the present invention that the skin- or hair-care compositions provide excellent moisturizing effectiveness, despite the fact that they contain no or low levels of insoluble emollient oils. "Colloidally-soluble" herein refers to particles in the usual colloidal size range, typically from 1 to 1000 nm, especially from 1 to 500 nm. In highly preferred embodiments, the compositions are substantially free of materials which are insoluble or not colloidally-soluble in distilled water at 20° C. Such materials include many conventional emollient materials such as hydrocarbon oils and waxes, glyceride esters, alkyl esters, alkenyl esters, fatty alcohols, certain fatty alcohol ethers and fatty acid esters of ethoxylated fatty alcohols, sterols extracted from lanolin, lanolin esters, wax esters, beeswax derivatives, vegetable waxes, phospholipids, sterols and amides. The compositions can, however, contain low levels of insoluble ingredients added, for example for visual-effect purposes, e.g. thermochromic liquid crystalline materials such as the microencapsulated cholesteryl esters and chiral nematic (non-sterol) based chemicals such as the (2-methylbutyl)phenyl 4-alkyl(oxy) benzoates available from Hallcrest, Glenview, Ill. 60025, U.S.A. The addition of a proportion of insoluble silicone component is also envisaged herein, as described in detail below.

Other than the polyethyleneglycol glyceryl fatty ester surfactants, the compositions of the invention have no need of and are preferably substantially free of surfactant materials which are conventionally added to cosmetic cream and lotion compositions in order to emulsify a water-insoluble oily phase. Again, "substantially free" means less than about 1%, preferably less than about 0.1% of the indicated materials. Such emulsifiers include ethoxylated fatty acids, ethoxylated esters, phosphated esters, ethoxylated fatty alcohols, polyoxyethylene fatty ether phosphates, fatty acid amides, acyl lactylates, soaps, etc.

As mentioned above, the compositions of the invention can additionally comprise from about 1.0% to about 10% by weight of a silicone component consisting essentially of (i) a silicone having a molecular weight of from about 200,000 to about 600,000 selected from dimethiconol, fluorosilicone and dimethicone and mixtures thereof; and (ii) a silicone-based carrier having a viscosity from about 0.65 mPa.s to about 100 mPa.s;

wherein the ratio of i) to ii) is from about 10:90 to about 20:80 and wherein said silicone component has a final viscosity of from about 500 mpa.s to about 10,000 mpa.s.

Dimethiconol-based silicones suitable for use herein have the chemical structure (II):

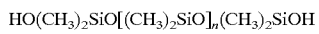

where n is from about 2700 to about 4500, preferably from about 3200 to about 4300 and most preferably from about 4000 to about 4300. The dimethiconol has a molecular weight of from about 200,000 to about 300,000, preferably from about 240,000 to about 260,000 and most preferably about 250,000.

The fluorosilicones useful herein have a molecular weight of from about 200,000 to about 300,000, preferably from about 240,000 to about 260,000 and most preferably about 250,000.

The dimethicones include silicone gums as described by Petrarch and others including U.S. Pat. No. 4,152,416, May 1, 1979 to Spitzer, et al, and Noll, Walter, *Chemistry and Technology of Silicones*. New York: Academic Press 1968. Also describing silicone gums are General Electric Silicone Rubber Product Data Sheets SE 30, SE 33, SE 54 and SE 76.

"Silicone gum" materials useful herein denote high molecular weight materials having a molecular weight of from about 200,000 to about 600,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

The silicone-based carriers suitable for use herein include certain silicone fluids.

The silicone fluid can be either a polyalkyl siloxane, a polyaryl siloxane, a polyalkylaryl siloxane or a polyether siloxane copolymer and is present at a level of from about 0.1% to about 10.0%, preferably from about 0.5% to about 5.0% by weight of the silicone component. Mixtures of these fluids can also be used and are preferred in certain executions.

The polyalkyl siloxane fluids that can be used include, for example, polydimethylsiloxanes with viscosities ranging from about 5 to 600,000 mm$^2$.s$^{-1}$ at 25° C. These siloxanes are available, for example, from the General Electric Company as the Viscasil (RTM) series and from Dow Corning as the Dow Corning 200 series. The essentially non-volatile polyalkylarylsiloxane fluids that can be used include, for example, polymethylphenylsiloxanes, having viscosities of about 0.65 to 30,000 mm$^2$.s$^{-1}$ at 25° C. These siloxanes are available, for example, from the General Electric Company as SF 1075 methyl phenyl fluid or from Dow Corning as 556 Cosmetic Grade Fluid.

Also suitable for use herein are certain volatile cyclic polydimethylsiloxanes having a ring structure incorporating from about 3 to about 7 $(CH_3)_2SiO$ moieties.

The viscosity can be measured by means of a glass capillary viscometer as set forth in Dow Corning Corporate Test Method CTM0004, Jul. 29, 1970. Preferably the viscosity ranges from about 3500 mm$^2$.s$^{-1}$ to about 100,000 mm$^2$.s$^{-1}$.

The most preferred silicone component for use herein is a dimethiconol gum having a molecular weight of from about 240,000 to about 260,000 along with a silicone carrier with a viscosity of about 5 mm$^2$.s$^{-1}$. An example of this silicone component is Dow Q2-1403 fluid (85% 5 mm$^2$.s$^{-1}$ Dimethyl Fluid/15% Dimethiconol) available from Dow Corning.

A number of additional water-soluble materials can be added to the compositions of the invention. A highly preferred additional ingredient from the viewpoint of skin feel and tack reduction is a fluid copolymer of ethylene oxide and propylene oxide having a viscosity in the range of from 55 to 300,000 Saybolt Universal Seconds [S.U.S.], preferably from 100 to 2,000 S.U.S. at 38° C., for example Ucon Fluid 75-H 450.

Another optional but preferred ingredient of the compositions of the invention is trimethylglycine, otherwise sometimes known as betaine. Trimethylglycine is valuable herein from the viewpoint of providing improved skin feel and tack reduction. In the present compositions, trimethylglycine is preferably present at a level of from about 1% to about 10% by weight, preferably from about 3% to about 7% by weight.

The compositions of the invention can also contain from about 0.1% to about 10%, preferably from about 1% to about 5% of a panthenol moisturizer. The panthenol moisturizer can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex. Highly preferred from the viewpoint of skin care and tack reduction is D-panthenol.

The compositions of the present invention can additionally comprise from about 0.001% to about 0.5%, preferably from about 0.002% to about 0.05%, mores preferably from about 0.005% to about 0.02% by weight of carboxymethylchitin. Chitin is a polysaccharide which is present in the integument of lobsters and crabs and is a mucopolysaccharide having beta (1–4) linkages of N-acetyl-D-glucosamine. Carboxymethylchitin is prepared by treating the purified chitin material with alkali followed by monochloracetic acid. It is sold commercially in the form of a dilute (approximately 0.1% to 0.5% by weight) aqueous solution under the name Chitin Liquid available from A & E Connock Ltd., Fordingbridge, Hampshire, England.

Other optional materials include keratolytic agents such as salicylic acid; proteins and polypeptides and derivatives thereof; water-soluble or solubilizable preservatives such as Germall 115, methyl, ethyl, propyl and butyl esters of hydroxybenzoic acid, EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.2% to about 5%); soluble or colloidally-soluble moisturising agents such as hylaronic acid and starch-grafted sodium polyacrylates such as Sanwet (RTM) IM-1000, IM-1500 USA and described in U.S. Pat. No. 4,076,663; colouring agents; perfumes and perfume solubilizers etc. Water is also present at a level of from about 50% to about 99.2%, preferably from about 80% to about 95% by weight of the compositions herein.

The pH of the compositions is preferably from about 4 to about 9, more preferably from about 4.5 to about 7, the pH being controlled where necessary through the use of pH buffers such as citric acid/sodium citrate.

The invention is illustrated by the following examples.

EXAMPLES I to V

|  | I | II | III | IV | V |
|---|---|---|---|---|---|
| D-Panthenol | 2 | — | — | — | 3 |
| Glycerine | 3 | 2 | 6 | 5 | 3 |
| Lubrajel Oil | 0.5 | 0.5 | 2.0 | 0.5 | 0.5 |
| Lubrajel DV | 5.0 | 1.0 | — | 5.0 | — |
| PEG-6 capric/caprylic glyceride | 2.00 | 3.0 | 1.0 | 4.0 | 5.0 |
| PEG-70 evening primrose glyceride | 1.00 | — | 2.0 | — | — |
| Q2 1403 Silicone | — | 3.00 | — | — | — |
| Carbopol 981 | 0.5 | 0.4 | 0.6 | 0.4 | 0.4 |
| Chitin Liquid | 0.006 | — | — | — | — |
| Pemulen TR-1 | — | 0.4 | — | 0.3 | 0.3 |
| Sodium hydroxide | 0.25 | 0.25 | 0.3 | 0.2 | 0.2 |
| Methyl parabens | 0.1 | 0.1 | 0.1 | 0.1 | 0.1 |
| Germall 115 | 0.2 | — | 0.2 | — | 0.2 |
| Hexylene glycol | 2 | — | — | — | 2 |
| Phenoxyethanol | — | — | — | 0.25 | — |
| Butylene Glycol | 2.0 | 2.0 | 2.0 | — | — |
| Perfume Oils | 0.001 | 0.0015 | 0.001 | 0.001 | 0.0006 |
| Deionised Water |  |  | To 100 |  |  |

The compositions are made by mixing at ambient temperature.

The compositions display improved moisturization, skin feel, skin care and residue characteristics together with excellent emolliency, rub-in and absorption characteristics.

What is claimed is:

1. A skin or hair care composition in the form of an aqueous gel or lotion comprising:
   (a) from about 0.5% to about 20% by weight of a polyhydric alcohol humectant;
   (b) from about 0.1% to about 10% by weight of a water-soluble polyglycerylmethacrylate lubricant;
   (c) from about 0.1% to about 20% by weight of a hydrophilic gelling agent; and
   (d) from about 0.1% to about 10% by weight of a surfactant component comprising at least two polyethyleneglycol glyceryl fatty ester surfactants having the formula:

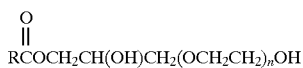

wherein n, the degree of ethoxylation, is from about 2 to about 200, wherein n in one of the two polyethyleneglycol glyceryl fatty esters is from about 30 to about 80, and wherein R comprises an aliphatic radical having from about 5 to about 25 carbon atoms.

2. A composition according to claim 1 comprising from about 1% to about 10% by weight of the polyhydric alcohol humectant.

3. A composition according to claim 1 wherein the polyglycerylmethacrylate lubricant is a hydrate or clathrate formed by the reaction of sodium glycerate with a methacrylic acid polymer.

4. A composition according to claim 3 wherein the polyglycerylmethacrylate lubricant is selected from lubricants having a viscosity (neat) of less than about 5000 mpa.s, lubricants having a viscosity (neat) of at least about 50,000 mpa.s, and mixtures thereof, viscosities being measured with a Brookfield RVT, at 20° C.

5. A composition according to claim 4 comprising from about 0.2% to about 8% by weight of the polyglycerylmethacrylate lubricant.

6. A composition according to claim 1, comprising from about 0.5% to about 8%, by weight, of the polyethyleneglycol glyceryl fatty ester surfactant component.

7. A composition according to claim 1 wherein the weight ratio of water-soluble polyglycerylmethacrylate lubricant to polyethyleneglycol glyceryl fatty ester surfactant is from about 5:2 to about 1:10,.

8. A composition according to claim 7 wherein the water-soluble polyglycerylmethacrylate lubricant comprises a mixture of a first lubricant component having a viscosity (neat) of from about 200 to about 5000 mPa.s and a second lubricant component have a viscosity (neat) of at least about 200,000 mPa.s wherein the weight ratio of the first lubricant component to the second lubricant component is from about 5:1 to about 1:20.

9. A composition according to claim 1 having a viscosity (25° C., neat, Brookfield RVT, Spindle No. 5) of from about 4000 to about 300,000 mPa.s,.

10. A composition according to claim 1 wherein the gelling agent has a viscosity (1% aqueous solution, 20° C., Brookfield RVT) of at least about 4000 mPa.s,.

11. A composition according to claim 10 wherein the gelling agent comprises a carboxyvinyl polymer.

12. A composition according to claim 10 wherein the gelling agent comprises a hydrophobically-modified crosslinked polymer of acrylic acid having amphipathic properties.

13. A composition according to claim 10 comprising from about 0.2% to about 2%, of the gelling agent.

14. A composition according to claim 1 which is substantially oil-free.

15. A composition according to claim 1 additionally comprising from about 1.0% to about 10% by weight of a silicone component consisting essentially of
   (i) a silicone having a molecular weight of from about 200,000 to about 600,000 selected from dimethiconol, fluorosilicone and dimethicone and mixtures thereof; and
   (ii) a silicone-based carrier having a viscosity from about 0.65 mPa.s to about 100 mPa.s;
   wherein the ratio of i) to ii) is from about 10:90 to about 20:80 and wherein said silicone component has a final viscosity of from about 500 mPa.s to about 10,000 mPa.s.

16. A composition according to claim 11 wherein said carboxyvinyl polymer is a collodially water-soluble polymer of acrylic acid cross-linked with from about 0.75% to about 2% of a cross-linking agent selected from polyallyl sucrose and polyallyl pentaerythriol.

17. A composition according to claim 2 comprising from about 2% to about 5% by weight of the polyhydric alcohol humectant.

18. A composition according to claim 5 comprising from about 0.5% to about 6% by weight of the polyglycerylmethacrylate lubricant.

19. A composition according to claim 8 wherein the water-soluble polyglycerylmethacrylate lubricant comprises a mixture of a first lubricant component having a viscosity (neat) of from about 700 to about 900 mPa.s and a second lubricant component have a viscosity (neat) of at least about 500,000 mPa.s wherein the weight ratio of the first lubricant component to the second lubricant component is from about 2:1 to about 1:15.

20. A composition according to claim 1, wherein n in the other of the two polyethyleneglycol glyceryl esters is from about 4 to about 20.

* * * * *